United States Patent [19]

Saros

[11] Patent Number: 4,517,302
[45] Date of Patent: May 14, 1985

[54] CONTINUOUS FLOW METERING APPARATUS

[75] Inventor: Stephen Saros, Wantagh, N.Y.

[73] Assignee: Technicon Instruments Corporation, Tarrytown, N.Y.

[21] Appl. No.: 441,720

[22] Filed: Nov. 15, 1982

[51] Int. Cl.³ .................. G01N 1/14; G01N 35/08
[52] U.S. Cl. .................. 436/180; 73/864.22; 422/82; 422/100; 436/53
[58] Field of Search ........... 73/861.05, 864.11–864.12, 73/864.15–864.18, 864.21–864.25; 137/154, 551; 204/406–409; 222/154; 324/439, 442, 443, 450, 453; 364/510; 422/81, 82, 100; 436/43, 47, 52–55

[56] References Cited

U.S. PATENT DOCUMENTS

| 3,143,393 | 8/1964 | de Seguin des Hons .... 73/864.11 X |
| 3,250,113 | 5/1966 | Rush .......................... 324/439 X |
| 3,383,310 | 5/1968 | Ammer ....................... 324/443 X |
| 3,583,232 | 6/1971 | Isreeli et al. ................ 422/103 X |
| 3,929,413 | 12/1975 | Young et al. ............... 436/53 |
| 4,121,466 | 11/1978 | Reichler et al. ............ 73/864.22 |
| 4,253,846 | 3/1981 | Smythe et al. ............. 436/53 |
| 4,358,423 | 11/1982 | Nedetzky .................. 422/81 X |
| 4,398,894 | 8/1983 | Yamamoto ................ 422/82 X |

Primary Examiner—Barry S. Richman
Assistant Examiner—Michael S. Gzybowski
Attorney, Agent, or Firm—S. P. Tedesco

[57] ABSTRACT

Continuous flow metering apparatus and methods using liquid position sensors in conjunction with flow-stopping valves control (meter) fluid, e.g. sample/reagent-/air, aspiration into a single conduit, such as in a continuous flow system. Air or other gas separates selected ones of the liquid segments. The volume of the aspirated segment is established by sensing a flow parameter of the segmented stream of a selected one of the sensors. A pulse is generated by the sensors (detectors), for example due to the change of light intensity at a liquid/air interface traversing the conduit. The signal pulse from a sensor causes the actuation of a selected one of the valves and stops aspiration (flow) of the liquid by traversing the flow path in the conduit through an air segment. The valve cuts through air only. Therefore, the body of the valve does not contact reagent or sample liquid by this action and the risk of carryover contamination is avoided. With the aspiration cycle completed, the input end of the conduit, e.g. an aspirating probe, can consequently be immersed in different media and the cycle repeated.

23 Claims, 6 Drawing Figures

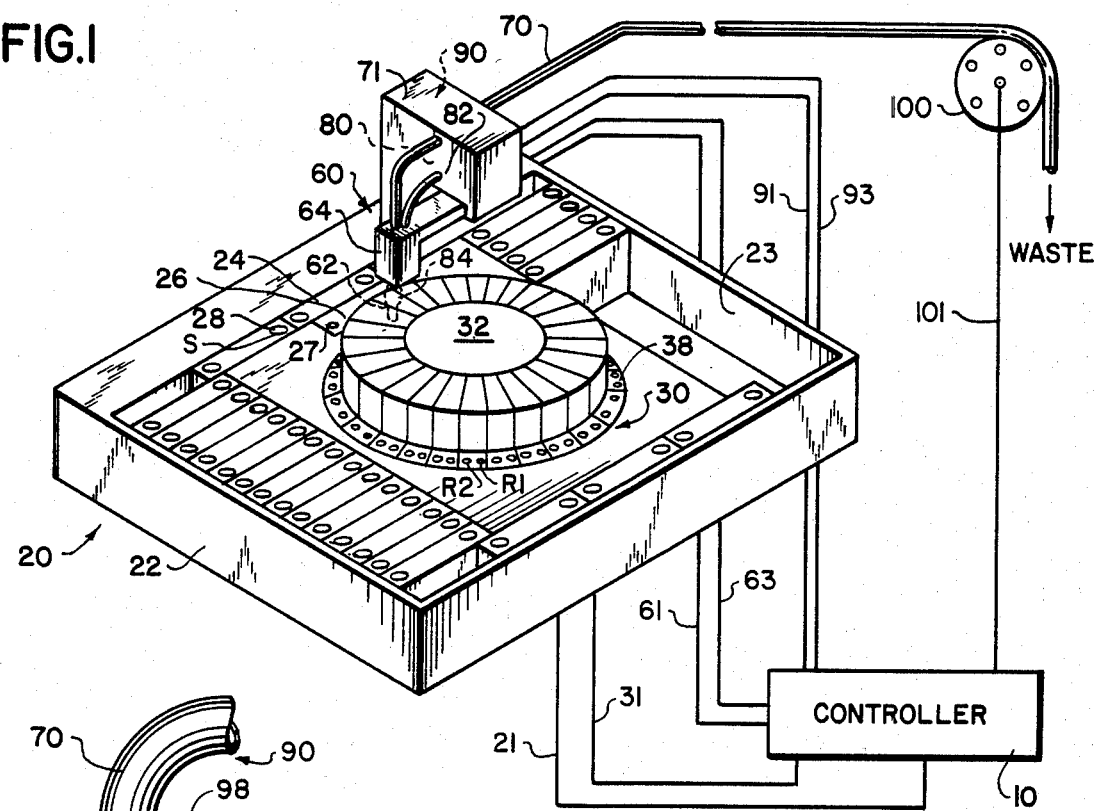
FIG.1
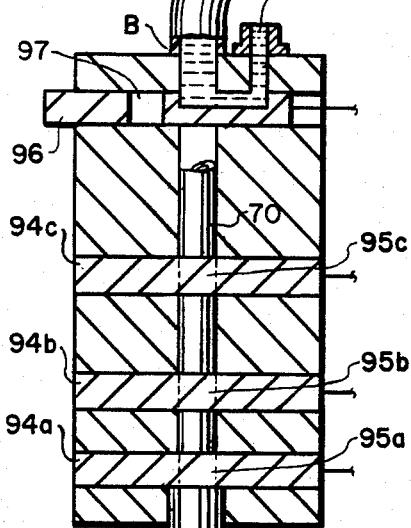
FIG.2
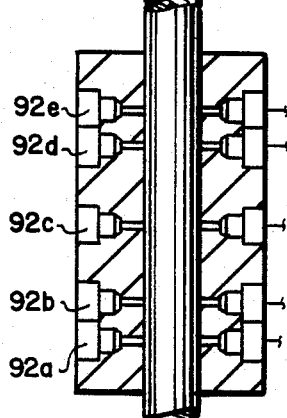
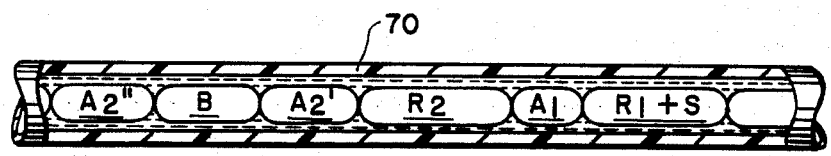
FIG.4

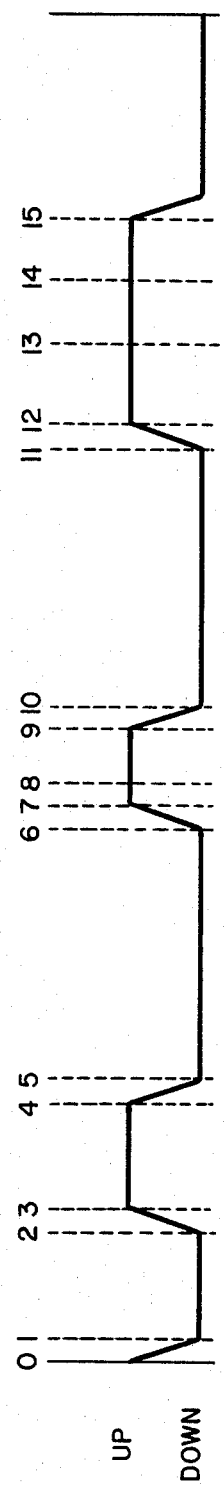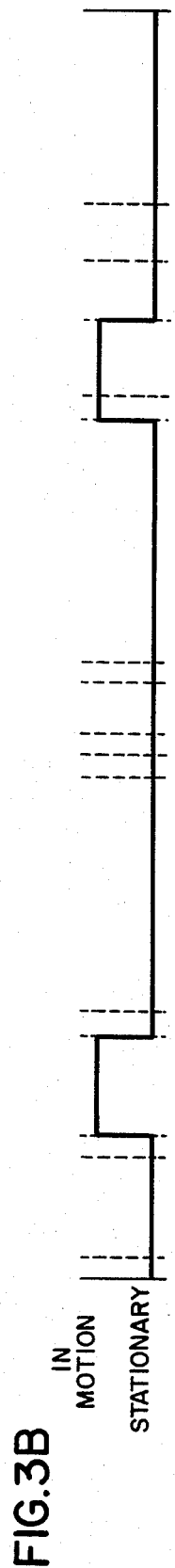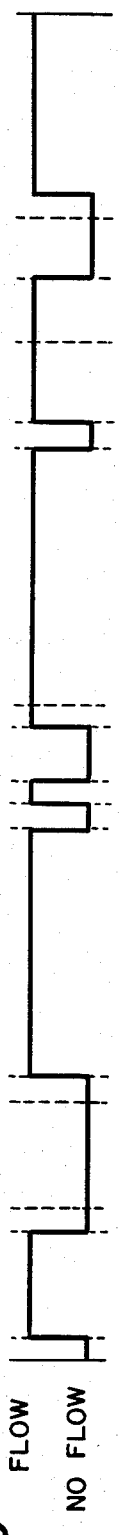

CONTINUOUS FLOW METERING APPARATUS

BACKGROUND OF THE INVENTION

1. Field of Invention

The present invention relates to a fluid handling system, apparatus and method. It is particularly useful for sequential introduction of fluids, including gases, liquid samples and processing liquids such as reagents or diluents, into continuous flow analyzers.

2. Brief Description of the Prior Art

Automated apparatus for the analysis of liquid samples as a flowing stream was disclosed by Skeggs in U.S. Pat. Nos. 2,797,149 and 2,879,141, both assigned to the instant assignee. In this basic apparatus, the liquid samples are sequentially aspirated from storage containers into a conduit, each sample being separated from the next successive sample by a segment of air. Air is introduced into the conduit to segment each individual sample to promote intrasample mixing and between successive samples to prevent intersample contamination. As illustrated by Ferrari in U.S. Pat. No. 2,933,293, also assigned to the instant assignee, a junction in the conduit continually introduces a processing liquid, such as a reagent, into the alternating sequence of air and sample segments. Ferrari et al, U.S. Pat. No. 3,109,713, assigned to the instant assignee, also discloses an analysis apparatus in which processing fluids, such as reagents, are continuously introduced into a stream of alternating air and sample segments, as shown at the juncture of conduits 42 and 44 in FIG. 1.

Smythe et al, U.S. Pat. No. 3,479,141, likewise assigned to the instant assignee, discloses a transport system for automatic analysis apparatus in which a series of aqueous liquid samples are processed as a flowing fluid with substantially no contamination between segments. A fluoropolymer conduit and intersample carrier segments of silicone are used. The silicone encapsulates the aqueous liquid segments. Thus, the intermixing of successive liquid segments is substantially completely eliminated.

Bannister, et al, U.S. Pat. No. 3,759,667 discloses a method and apparatus for aspirating a liquid sample followed by increments of diluent, introduced through a different inlet, in precise volumetric ratio to the sample volume, particularly for use in automated analyzers. The apparatus includes an aspirating probe, having a complex apparatus for introducing diluent through a diluent chamber, which vertically reciprocates from a lower, aspirating position to an upper position in which diluent is introduced through the diluent chamber, and thereafter to an intermediate position in which air is aspirated. The aspiration sequence disclosed is (1) serum; (2) diluent; (3) air; (4) diluent; (5) air; (6) diluent, and presumably (7) air. This column of fluids is passed along a conduit by the vacuum action of a downstream proportional pump, through a vertical mixing stage and into an aliquot splitting section for dispensing. This patent teaches that it is necessary to restrain the acceleration which arises when the probe end moves from aspirating relatively heavy fluid to aspirating air. A controlled pulse of air pressure is introduced to compensate for this acceleration.

A first sensor, such as an optical sensor, detects either the diluent/air or serum/air interface and is positioned on the conduit at a distance from the probe tip such that the precise volume of sample is aspirated to that point. A second sensor is positioned further along the conduit and is separated from the first sensor by a helical mixing coil, such that the volume between it and the probe tip is equal to the desired total volume of sample, air and diluent. Signals from these sensors, operating together with and interdependent upon signals from a timing device, are used to control the movement of the aspirating probe and thereby to control the volumetric ratio between the aspirated serum and the aspirated diluent. This patent does not disclose or suggest any possible use for a series of values operating in coordination with the sensors, let alone their use to establish or create discrete fluid segments. In conventional fluid metering systems such as this, positive displacement (pistons) or peristaltic pumps are used, the travel of a piston or roller thus determining the accuracy of flow rate, and, therefore, aspirated segment volume. Control of the creation of such fluid segments is not separated from the control of fluid stream passage by the pump. Also, the metering precision, as well as the driving force, is controlled by the fluid pumping mechanism.

Young, et al, U.S. Pat. No. 3,929,413 discloses a system for forming and transporting small, discrete measured quantities (slugs) of fluid in a conduit, such as in automated chemical analysis apparatus. These slugs are formed by detecting, with suitable detectors, the leading meniscus of a fluid in the conduit and automatically actuating a single, complex valve which is upstream of, e.g., closer to the aspirator than, the detector(s). Essentially, this valve is a magnetic actuator enclosed in a non-magnetic body and responsive to a pair of magnetic fields produced by electrical coils located respectively on inlet and outlet sides of the valve chamber. These slugs are passed through the conduit by a push and pull combination of vacuum upon the leading meniscus and air pressure upon the trailing meniscus which depends upon operation of the valve to, in effect, open the conduit wall and introduce pressurized air. A vacuum applied proximate the dispensing end draws the fluid into and through a probe until a predetermined volume of fluid has been introduced. The flow-controlled metering valve is then actuated, the valve introduces pressurized air to further provide and control the motive force for the fluid stream, and thus the fluid slug is transported by a combination of vacuum and air pressure as described. The patent teaches that this is to be preferred over peristaltic pumping which is independent of valving or detection of fluid stream passage. Further, the motive force here disclosed is neither continuous nor uniform, as evidenced by the configuration of vacuum control valve 211 in FIG. 3a. In fact, it is taught that flow velocity must be measured because of the variations in flow rate caused by slugs of different materials.

As is further disclosed by Young, et al, one or more metering detectors are spaced along the fluid conduit and respond to the passage of the leading fluid meniscus therethrough to automatically close a flow-control valve and form a slug of known volume. Plural detectors are spaced along the conduit to produce slugs of different volume, only one valve being used even with a plurality of detectors. This flow-control valve intersects the stream of liquid and this presents a major risk of carryover contamination.

Each of the above patents have provided an advance of one sort or another in fluid handling, particularly the introduction of samples to automated analysis systems. This end has been widely recognized as a major consideration in the improvement of continuous-flow systems in particular because of their high throughput. Thus, the combined references provide a significant background literature on the technology of samplers for continuous-flow analysis systems.

SUMMARY OF THE INVENTION

A new concept in controlled fluid handling has been developed, primarily for use in clinical chemistry analysis systems. All of the samples to be assayed and all of the reagents required are introduced through a single aspirating probe. All tests for every sample are processed through a single transmission channel. In the apparatus of the invention, the metering function is separated from the driving (pumping) mechanism. The aspirated volume (accuracy) is directly monitored on the fluid at the front-end of the system using position sensors, such as photodetectors. The driving (pumping) unit is positioned downstream therefrom. Thus, these two functions are independently achieved by two separate mechanisms, reducing the criticality of combined requirements. Continuous-flow metered aspiration is accomplished with high accuracy and without the gradual degradation of performance as in the case where it is under the control of peristaltic pumping which is used without other means for controlling the volumes of fluid segments introduced.

New apparatus and methods are disclosed using liquid position sensors in conjunction with flow-stopping valves to control (meter) fluid, e.g. sample/reagent/air, aspiration through a single aspirating probe into a single conduit. Air or other gas separates the liquid segments. The volume of the aspirated segment is established by sensing a flow parameter of the segmented stream at a selected one of the sensors. The multiple sensors and valves can generate different segment patterns of air/liquid volumes. A pulse is generated by the detector, for example due to the change of light intensity at the liquid-air interface transversing the conduit. The signal pulse from a sensor causes the actuation of a selected one of the valves and stops aspiration (flow) of the liquid by traversing the flow path in the conduit through an air segment. The valve cuts through air only. Therefore, the body of the valve does not contact reagent or sample liquid by this action and the risk of carryover contamination is avoided. With the aspiration cycle completed, the input end of the conduit, e.g. an aspirating probe can consequently be immersed in different media and the cycle repeated.

As such, the present invention provides apparatus for metering the introduction of a sequence of fluid segments into a conduit, which apparatus comprises (a) means disposed along said conduit for sensing a flow parameter of an alternating sequence of gas and liquid stream segments, and (b) means for stopping stream introduction, disposed downstream of and individually responsive to sensing of said flow parameter by selected ones of said sensing means, said stopping means being disposed so as to intersect a preceding gas segment at different positions along said conduit. In a preferred embodiment, this apparatus for metering the introduction of a sequence of fluid segments into a conduit comprises (a) a series of five sensors sequentially disposed along said conduit at different positions relative to the point of introduction of said fluid segments and adapted to sense, e.g. optically, segment interfaces of an alternating sequence of gas and liquid stream segments; (b) a series of three shear valves positioned downstream of and individually responsive to sensing of an interface by a selected one of said sensors to intersect a preceding gas segment; and (c) a fourth shear valve positioned downstream of said series of three shear valves, said fourth shear valve being adapted simultaneously to stop the introduction of said sequence of fluid segments and to introduce a fluid into a gas segment of said alternating sequence of gas and liquid stream segments.

The invention also provides a method for metering the introduction of a sequence of fluid segments into a conduit, which method comprises (a) sensing a flow parameter of an alternating sequence of gas and liquid stream segments along said conduit; and (b) stopping stream introduction downstream of and in response to sensing of said flow parameter by selected ones of said sensing means to intersect a preceding gas segment at different positions along said conduit. In a preferred embodiment of this method, sensing comprises sensing, e.g. optically, segment interfaces of an alternating sequence of gas and liquid stream segments.

BRIEF DESCRIPTION OF THE DRAWINGS

FIG. 1 illustrates a portion of a continuous flow system incorporating a preferred embodiment of the metering apparatus of the invention;

FIG. 2 is an enlarged view of the metering apparatus referred to in FIG. 1;

FIGS. 3A-3C are timing diagrams, each of which illustrates the operating status of a particular system parameter during a complete "test package" aspiration sequence (cycle); and FIG. 4 illustrates the sequence of separated segments provided in accordance with a preferred method using the metering apparatus of FIG. 2.

DESCRIPTION OF THE PREFERRED EMBODIMENTS

Although specific terms are used in the following description for clarity, they refer only to the particular embodiment(s) selected for illustration, and are not intended to limit the scope of the invention.

The metering apparatus of the present invention is particularly suitable for continuous flow analyzers which are used to detect an analyte in a liquid sample. Sample fluids on which tests are performed include biological, physiological, industrial, environmental and other types of liquids. Of particular interest are biological fluids such as whole blood, serum, plasma, urine, cerebrospinal fluid, broth and other culture media and supernatants as well as fractions of any of them. Physioloigical fluids of interest include infusion solutions, buffers, preservative or antimicrobial solutions and the like. Industrial liquids include fermentation media and other processing liquids used, for example, in the manufacture of pharmaceuticals, dairy products and malt beverages. Other sources of sample fluid which are tested by conventional methods are contemplated as within the meaning of this term.

Referring now to FIG. 1, controller 10 is a general purpose digital computer with a stored (fixed) program which can be associated with a user console (not shown) and recorder (not shown). The user console conventionally includes a cathode ray tube (CRT) terminal and keyboard and the recorder conventionally includes a printer for recording the test data of each analysis. Controller 10 instructs, monitors and controls the sequence and coordination of system operations, as more fully described below, as well as calculates and monitors the quality of results and provides data output in a variety of formats.

Sample assembly 20 includes sample table 22 which holds a plurality of sample carrier blocks 24 and a shuttle carrier 26. Each such carrier block 24 carries a plurality of sample vessels 28 containing a body fluid sample S, e.g. serum. As directed by controller 10 along lead 21, sample blocks 24 are sequentially moved in a clockwise direction to a position where the appropriate sample vessel 28 is presented for aspiration. When the system has completed the necessary aspiration of sample S from all of the sample vessels 28 of a particular sample carrier block 24, that sample carrier block 24 is moved to a holding area 23 of sample table 22.

Reagent assembly 30 includes reagent turntable 32 connected to bidirectional rotational drive means (not shown). The drive means is activated by controller 10 along lead 31 connected to the non-illustrated drive means to impart a metered rotation of reagent turntable 32 to present a selected reagent dispenser 38 for aspiration. Reagent turntable 32 is provided with one row of reagent dispensers 38, each of which contains the components necessary to present the first reagent $R_1$ and the second reagent $R_2$ of two reagents necessary for reaction with a sample S, for dispensing. The drive means rotates turntable 32 slightly after aspiration of first reagent $R_1$ to present the second reagent $R_2$ for aspiration. Reagent dispenser 38 is a preferred embodiment of the reagent package which is the subject of cofiled U.S. patent application Ser. No. 441,880 and assigned to the instant assignee.

Probe assembly 60 includes probe 62 which aspirates sample, reagent and air into conduit 70 and is preferably made of a solid fluoropolymer. Probe 62 is carried at one end of probe arm 64, the other end of which is connected to bidirectional linear drive means (not shown). Directed by controller 10, along lead 61, the drive means imparts bidirectional horizontal movement of probe arm 64 to position probe 62 over a selected sample vessel 28, ancillary fluid vessel 27, containing calibrators or controls, or reagent dispenser 38 which has been presented for aspiration. Additionally, the drive means imparts bidirectional vertical movement, under control of controller 10 along lead 63, to probe tip 62 which is thereby lowered into sample vessel 28 or reagent dispenser 38 and, after aspiration, raised. Aspiration of fluids is effected by pumping means which is located at the downstream end of the system and is more fully described below. The aspirated liquid segments are passed along the conduit. Preferably, the inner surface of the conduit is coated with an immiscible liquid such as described in Smythe et al, U.S. Pat. No. 3,479,141 to prevent undesirable carryover contamination.

Housing 71 encloses an immiscible liquid dispenser assembly 80 which dispenses immiscible liquid, such as fluorocarbon, from applicator shroud 84 onto the outer surface of probe 62. The immiscible liquid preferentially wets and forms a continuous film over the outer and inner surfaces of probe 62, the inner surface of conduit 70 and other conduits of the system. In operation, probe 62 passes through a lens of immiscible fluid formed on the reagent liquid surface of reagent in reagent dispenser 38, as is fully described in the above-cited U.S. patent application Ser. No. 441,880.

Housing 71 encloses metering apparatus 90, in accordance with the present invention, which uses liquid position sensors in conjunction with flow-stopping valve(s) to control (meter) sample/reagent/air aspiration into a conduit of a continuous flow system. Multiple detectors (sensors) and valves can generate different segment patterns of air/liquid volumes. In a preferred embodiment, metering apparatus 90 aspirates, in order, (1) a sample to be analyzed, and (2) a first reagent, which combine in conduit 70 to form a first liquid segment, (3) a small segment of air, (4) a second reagent which constitutes a second liquid segment, and (5) a large segment of air. Controller 10 coordinates the operation of assembly 20, reagent assembly 30, probe assembly 60 and immiscible liquid IL dispenser assembly 80 with each other and with metering assembly 90, an example of which is described in more detail with reference to later drawings.

The reacted segments flow through conduit 70 and into a detector assembly (not shown). The detector assembly measures a characteristic of or other detectable response associated with the original sample by appropriate analytical techniques. Peristaltic pump 100 rotates under direction of controller 10, along lead 101, pulling test package fluids through conduit 70. This provides the motive force for pulling all fluids into and through the system. Fluids which pump 100 has pulled through the system are passed to waste. This system is more fully described in cofiled U.S. patent application Ser. No. 441,881 and assigned to the instant assignee.

As illustrated in detail by FIG. 2, metering assembly 90 includes a detector component which comprises an array of liquid position sensors 92a–92e, such as infrared light emitting diodes operating together with infrared photodetectors, and a valve component, positioned a specified distance downstream of the detector component, which comprises shear valves 94a–94c and buffer valve 96. Shear valves 94a–94c are respectively provided with cylindrical passageways 95a–95c having an inner diameter and wetting characteristics identical to those of the inner wall of conduit 70. When one of shear valves 94a–94c is "actuated", the body of the valve so actuated traverses the flow path of conduit 70 and creates a condition of no flow between the probe and the valve, i.e., stops the introduction of fluid into the probe, as well as blocking flow downstream of the valve. Buffer valve 96 includes valve port 97 and buffer injection port 98 which introduces buffer B from a reservoir (not shown) into the portion of conduit 70 downstream of buffer valve 96. When buffer valve 96 is "actuated", the body of buffer valve 96 traverses the flow path of conduit 70 and creates a condition of no flow between the probe and the valve, as described with respect to shear valves 94a–94c. Concurrently, in the actuated position, buffer injection port 98 opens into fluid contact with the portion of conduit 70 downstream therefrom, thus permitting continued downstream flow and resultant introduction of buffer B.

The volume of each aspirated segment is established by the position of a selected one of detectors 92a–92e, which it activates, relative to the point of aspiration. In summary, a signal, such as an electronic pulse, is generated by the appropriate one of detectors 92a–92e and is received by a programmed controller which actuates the appropriate one of valves 94a–94c and also buffer valve 96 to stop aspiration of fluid by traversing conduit 70 through an air segment. Since the valve cuts through air only, no fluid is contacted by the body of a valve because of this action and, this potential cause of carryover is avoided. As a selected air segment passes along conduit 70 at buffer valve 96, the valve is actuated to bisect the air segment and thus introduce buffer B through buffer injection port 98.

FIGS. 3A-3C are timing diagrams, each of which illustrates the operating status of a particular system parameter at a number of points (points 0-15) during the aspiration cycle which produces a complete "test package", points 0 and 15 corresponding to identical states of the apparatus. FIG. 3A illustrates the relative vertical position (designated "up/down") of the aspirating probe at each of the points during the cycle. FIG. 3B illustrates the two states of horizontal motion ("in motion") and stationary ("stationary") of the aspirating probe at each of the points during the cycle (e.g. probe access). FIG. 3C illustrates the presence of a fluid flow ("flow") or no flow ("no flow") through the probe at each of the points during the cycle.

Referring now to FIGS. 1-4 together, at the beginning of a test package aspiration sequence, probe 62 is positioned over sample vessel 28, there is no flow through probe 62, and a segment of buffer B has just been introduced into large air segment $A_2$ of a prior test package by buffer injection port 98 of buffer valve 96 (point 0).

The test package aspiration sequence begins with the lowering of probe 62 into sample vessel 28, and deactuation of buffer valve 96 to stop introduction of buffer B from a prior cycle, simultaneous with the beginning of sample S aspiration (point 1). Sample S aspiration continues until liquid position sensor 92e detects the leading edge of a second reagent segment $R_2$ of the preceding test package, corresponding to aspiration of the correct volume of sample S into conduit 70, and generates a pulse which causes actuation of shear valve 94a (point 2). Shear valve 94a is positioned such that actuation causes it to shear on the large air segment (not shown) of a preceding test package to prevent carryover. The large air segment is later divided, as more fully described below, to produce air segments $A_2'$ and $A_2''$, illustrated in FIG. 4.

Probe 62 is raised (point 3) and rotated over reagent dispenser 38 (point 4), which has been positioned as described with reference to FIG. 1, for aspiration therefrom of the appropriate first reagent $R_1$. Probe 62 is lowered, stop valve 94a is deactuated, and aspiration of reagent $R_1$ begins (point 5). This aspiration of reagent $R_1$ continues until level sensor 92b detects the leading edge of the segment of sample S in the test package being aspirated, whereupon it generates a pulse which causes actuation of shear valve 94b (point 6). Probe 62 is then raised, valve 94b is deactuated (point 7) and air is aspirated until the leading edge of sample S segment is detected by level sensor 92c, which generates a pulse to again cause actuation of shear valve 94b (point 8). Small air segment $A_1$ is thus created. To this point, the steps of the operating cycle have created segments $R_1+S$ and $A_1$ of a test package.

A different dispensing well of the same reagent dispenser 38 has been rotated into position for aspiration of second reagent liquid $R_2$ (point 9). Probe 62 is lowered, shear valve 94b is deactuated and aspiration of the reagent $R_2$ begins (point 10). The aspiration of reagent $R_2$ continues until level sensor 92a detects the leading edge of reagent $R_2$ segment in the test package being aspirated, whereupon it generates a pulse which causes actuation of shear valve 94c (point 11). Probe 62 is then raised (point 12) and moved over the same or a different sample vessel 28 for the aspiration of a next fluid package. Shear valve 94c is deactuated (point 13) and air is aspirated, to create large air segment $A_2$, until the leading edge of reagent $R_2$ segment is detected by level sensor 92d. A pulse is then generated to actuate buffer valve 96 (point 14).

When actuated, buffer valve 96 introduces a flow of buffer B from a conventional supply source or reservoir (not shown) into large air segment $A_2$. The introduction of buffer B bisects large air segment $A_2$ to produce two approximately equal bubbles, $A_2'$ and $A_2''$. A complete test package is thus created in conduit 70 by this operating sequence and, thereafter, flows to subsequent portions of the analytical system.

Referring in particular now to FIG. 4, a test package is established by the metering apparatus of FIG. 3 in the method described above. This test package includes, in order, a sample S segment which combines as shown with reagent $R_1$ segment, small air segment $A_1$, reagent $R_2$ segment and large air segment $A_2$, which is divided substantially into equal segments $A_2'$ and $A_2''$ by a segment of buffer B. A complete test package is thus created in a single channel continuous flow conduit, and, thereafter, flows to subsequent portions of the analytical system.

Although the invention has been described with particularity, one skilled in the field can resort to numerous changes in the details, combinations and arrangements of elements without departing from the scope of the invention.

What is claimed is:

1. A method for metering the introduction of a sequence of fluid segments into a conduit, which method comprises:

sensing a flow parameter of an alternating sequence of gas and liquid stream segments along a conduit; and stopping stream introduction along a conduit downstream of and in response to sensing of a flow parameter by selected ones of a series of flow stopping valves, each of which intersects a preceding gas segment at a different position during passage along said conduit.

2. The method of claim 1 wherein said sensing comprises sensing a flow parameter corresponding to the volume of each of the fluid segments being introduced.

3. The method of claim 1 wherein said sensing comprises sensing a flow parameter of a fluid package comprising an alternating sequence of gas and liquid stream segments.

4. The method of claim 1 wherein said sensing comprises sensing segment interfaces of an alternating sequence of gas and liquid stream segments.

5. The method of claim 1 wherein said stopping comprises intersecting at least one gas segment of a preceding alternating sequence of gas and liquid stream segments.

6. The method of claim 1 which further comprises introducing a fluid into a gas segment of said alternating sequence of gas and liquid stream segments.

7. The method of claim 6 wherein stopping the introduction of said sequence of fluid segments occurs simultaneously with the introduction of a liquid into a gas segment of said alternating sequence of gas and liquid stream segments.

8. A method for metering the introduction of test packages, which test packages comprise a sample and first reagent liquid segment, a first air segment, a second reagent liquid segment and a second air segment, each segment having a leading edge and each but the first test package follows a preceding test package into the inlet of a single conduit and having an alternating sequence of air and liquid segments therein, which method comprises;

(a) aspirating a sample liquid into an inlet of a conduit;

(b) sensing the leading edge of a second reagent segment of a preceding test package in said conduit with a fifth sensor of a series of five sensors sequentially disposed along said conduit at different positions increasingly downstream from said conduit inlet, said sensors sensing segment interfaces of an alternating sequence of gas and liquid stream segments;

(c) intersecting in response to said sensing of (b) the second air segment of a test package downstream of said preceding test package with the first valve of a series of three valves sequentially disposed along said conduit at different positions increasingly downstream of said sensors and individually responsive to sensing of an interface by a selected one of said sensors to intersect a preceding gas segment and thereby stop aspiration of fluid into the inlet of said conduit;

(d) aspirating a first reagent liquid into the inlet of said conduit;

(e) sensing the leading edge of the sample liquid aspirated in (a) with a second sensor of said series of sensors;

(f) intersecting in response to said sensing of (e) the second air segment of a preceding test package with a second of said valves thereby again stopping aspiration of fluid into the inlet of said conduit;

(g) aspirating a first air segment into the inlet of said conduit;

(h) sensing the leading edge of the sample liquid segment aspirated in (a) with a third of said series of sensors;

(i) intersecting in response to said sensing of (h) the second air segment of a preceding test package with said second valve;

(j) aspirating a second reagent liquid into the inlet of said conduit;

(k) sensing the leading edge of said second reagent liquid segment aspirated in (j) with a first of said sensors;

(l) intersecting in response to said sensing of (k) the second air segment of a preceding test package with a third of said valves;

(m) aspirating a second air segment into the inlet of said conduit;

(n) sensing the leading edge of said second reagent liquid segment aspirated in (j) with a fourth of said sensors; and (o) stopping in response to said sensing of (n) the aspiration of said second air segment.

9. The method of claim 8 wherein stopping the introduction of said second air segment comprises intersecting the large air segment of a preceding test package with a fourth valve positioned downstream of said series of three valves.

10. The method of claim 9 which further comprises introducing a liquid into the second air segment so formed.

11. The method of claim 10 wherein said introducing comprises bisecting said second air segment with a segment of said liquid.

12. The method of claim 10 wherein said introducing comprises introducing said liquid through an injection port in said fourth valve.

13. The method of claim 12 wherein introducing said liquid through an injection port in said fourth valve comprises bisecting said second air segment with a segment of said liquid.

14. An apparatus for metering the introduction of a sequence of fluid segments into a conduit having an inlet, which apparatus comprises;

means defining a conduit having an inlet means;

a series of sensing means disposed along said conduit for sensing a flow parameter of an alternating sequence of gas and liquid stream segments; and a series of flow stopping means for stopping stream introduction of a sequence of fluid segments into said conduit, said flow stopping means being disposed at different locations along and within said conduit downstream of and individually responsive to sensing of said flow parameter by selected ones of said sensing means, which flow stopping means each intersect a preceding gas segment at a different position during passage along said conduit.

15. The metering apparatus of claim 14 wherein said sensing means comprises means for sensing a flow parameter corresponding to the volume of each of the fluid segments being introduced.

16. The metering apparatus of claim 14 wherein said sensing means each comprises means for sensing a flow parameter of a fluid package comprising an alternating sequence of gas and liquid stream segments.

17. The metering apparatus of claim 14 wherein said sensing means comprise means for sensing segment interfaces of said alternating sequence of gas and liquid stream segments.

18. The metering apparatus of claim 14 which further comprises means for introducing a fluid into a gas segment of said alternating sequence of gas and liquid stream segments.

19. The metering apparatus of claim 14 wherein said stopping means comprises a series of valves to intersect at least one gas segment of a preceding alternating sequence of gas and liquid stream segments.

20. The metering apparatus of claim 19 wherein said stopping means comprises a series of valves to intersect a gas segment of at least one preceding fluid package comprising an alternating sequence of gas and liquid stream segments.

21. The metering apparatus of claim 14 wherein said stopping means includes at least one valve adapted to stop the introduction of fluid into the inlet of said conduit and to introduce a fluid into a gas segment of said alternating sequence of gas and liquid stream segments.

22. The metering apparatus of claim 21 wherein said one valve comprises means for stopping the introduction of fluid into the inlet of said conduit and to introduce a fluid into a gas segment of said alternating sequence of gas and liquid stream segments.

23. An apparatus for metering the introduction of a sequence of fluid segments into an inlet of a conduit, which apparatus comprises:

means defining a conduit having an inlet means;

a series of five sensors sequentially disposed along said conduit at different positions relative to said inlet means, said sensors comprising means for sensing segment interfaces of an alternating sequence of gas and liquid stream segments;

a series of three shear valves positioned downstream of and individually responsive to sensing of an interface by a selected one of said sensors to intersect a preceding gas segment; and a fourth shear valve positioned downstream of said series of three shear valves, said fourth shear valve being adapted simultaneously to stop introduction of said sequence of fluid segments into said inlet means and to introduce a fluid into a gas segment of said alternating sequence of gas and liquid stream segments.

* * * * *